(12) United States Patent
Nguyen et al.

(10) Patent No.: US 9,307,757 B2
(45) Date of Patent: Apr. 12, 2016

(54) MONOALKYL SULFOSUCCINATES IN PESTICIDE FORMULATIONS AND APPLICATIONS

(75) Inventors: Giao Vinh Nguyen, Friendswood, TX (US); Mark Alexander, Fort Worth, TX (US)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 663 days.

(21) Appl. No.: 13/394,368

(22) PCT Filed: Sep. 21, 2010

(86) PCT No.: PCT/EP2010/063900
§ 371 (c)(1),
(2), (4) Date: Mar. 6, 2012

(87) PCT Pub. No.: WO2011/036152
PCT Pub. Date: Mar. 31, 2011

(65) Prior Publication Data

US 2012/0172229 A1    Jul. 5, 2012

Related U.S. Application Data

(60) Provisional application No. 61/245,450, filed on Sep. 24, 2009.

(30) Foreign Application Priority Data

Oct. 16, 2009   (EP) .................................... 09173229

(51) Int. Cl.
*A01N 25/02* (2006.01)
*A01N 25/30* (2006.01)
*A01N 57/20* (2006.01)

(52) U.S. Cl.
CPC ................ *A01N 25/02* (2013.01); *A01N 25/30* (2013.01); *A01N 57/20* (2013.01)

(58) Field of Classification Search
CPC ....... A01N 25/30; A01N 25/00; A01N 25/02; A01N 57/20; A01N 2300/00
See application file for complete search history.

(56) References Cited

U.S. PATENT DOCUMENTS 3,915,903 A    10/1975  Wise
4,095,973 A *  6/1978  Maeda et al. ................. 504/350
5,491,125 A    2/1996   Albrecht et al.

FOREIGN PATENT DOCUMENTS

| EP | 1 093 722 A2 | 4/2001 |
| WO | WO 2007/059101 A2 | 5/2007 |
| WO | WO 2008/066611 A2 | 6/2008 |

OTHER PUBLICATIONS

European Search Report for 09173229.7; Completion Date Mar. 10, 2010.
International Search Report for PCT/EP2010/063900; Completion Date Mar. 31, 2011.

* cited by examiner

*Primary Examiner* — John Pak
*Assistant Examiner* — Nathan W Schlientz
(74) *Attorney, Agent, or Firm* — Alice C. Su

(57) ABSTRACT

The present invention comprises formulations for use as pesticides and their applications. The formulations include a monoalkylsulfosuccinnate as a hydrotrope. The pesticide may be a herbicide comprising glufosinate-ammonium.

17 Claims, 2 Drawing Sheets

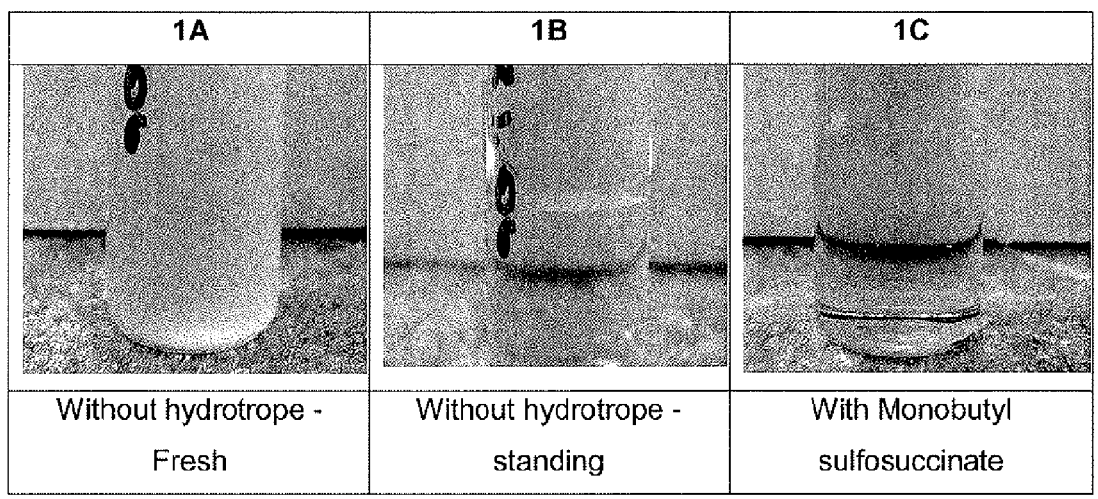
Figure 1: Clarity / uniformity of highload glufosinate –ammonium formulation containing ACAR 7053 as adjuvant

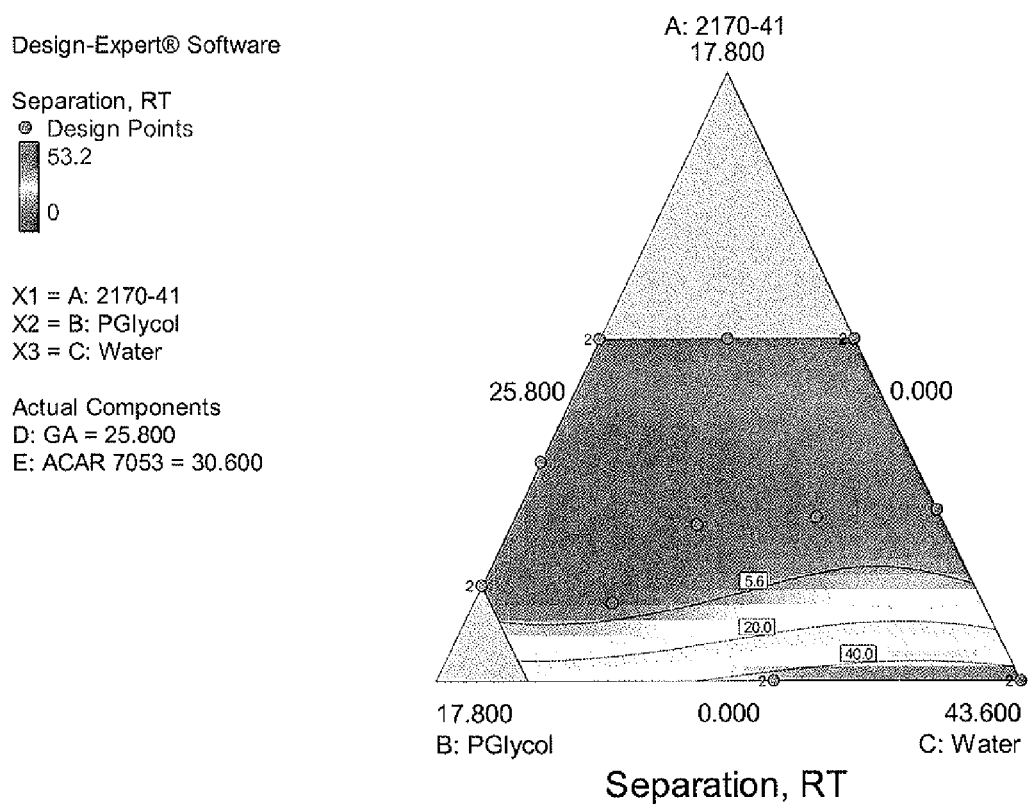
Figure 2: Designed experiment on function of sodium monobutylsulfosuccinate as hydrotrope.

MONOALKYL SULFOSUCCINATES IN PESTICIDE FORMULATIONS AND APPLICATIONS

FIELD OF THE INVENTION

The present invention relates to the use of monoalkylsulfosuccinates as hydrotropes in pesticide formulations and applications of such formulations.

BACKGROUND OF THE INVENTION

The agricultural chemical formulator has the difficult task of creating a product that balances bioefficacy, toxicity, cost, shelf life and user friendliness.

Of particular importance to the activity of an agricultural formulation is the ability of an aqueous solution to spread evenly over a surface, the so-called wetting ability, and the effective uptake of the active ingredient by the plant to be treated. For example, in agricultural formulations, efficacy benefits from a good wetting of the plant surface and uptake of the active ingredient.

Adjuvants are added to agricultural formulations to improve activity, thereby reducing the amounts of active ingredients necessary, resulting in lower formulation cost. They generally take the form of surface-active or salt-like compounds and, depending on their mode of action, they are classified as modifiers, actuators, fertilizers and/or pH buffers.

Surfactants are generally regarded as modifiers and/or actuators as they improve wetting properties and uptake of the active ingredients in the agricultural formulation. Additionally, some surfactants improve the solubility of active ingredients in formulations thereby eliminating serious issues such as product separation and/or crystallization.

Anionic, cationic, amphoteric and nonionic surfactants are all known and used in agricultural applications depending on the desired effect. For example, nonionic surfactants are known to be good wetting agents, and are often present in agricultural formulations. Many nonionic surfactants are not soluble enough in solutions with a high amount of electrolytes, such as alkali and/or alkaline complexing agents, salts, and the like and therefore need the presence of a hydrotrope to improve the solubility. A hydrotrope is a compound that solubilises hydrophobic compounds in aqueous solutions. A number of hydrotropes for nonionic surfactants have been described in various publications. Examples of such hydrotropes are ethanol, sodium xylene sulphonate, sodium cumene sulphonate, alkyl glycosides, and phosphated alkoxylated alcohols.

Pesticide formulations are becoming more complex and concentrated, with an increase in active loading, number of actives used in a formulation or the inclusion of adjuvants, such as surfactants. Those changes lead to a reduction in the water used in certain kinds of formulations, such as soluble liquids, leading to solubility issues within the formulation. A specific example is with glufosinate-ammonium. Glufosinate-ammonium is a water soluble, phosphinic acid based herbicide used for broad spectrum weed control. Early uses of the herbicide were for non-selective applications but tolerant crops have been engineered so applications now include food crops. The adjuvant used in combination with glufosinate-ammonium is typically an alcohol ether sulfate which is neutralized to form a sodium salt but the ammonium salt can also be used, and the adjuvant is formulated in-can with the herbicide. The ratio of pesticide to adjuvant can range from 1:1 to 1:5. As the ratio of pesticide to adjuvant moves closer to 1:1, the compatibility of the adjuvant becomes more challenging.

Application culture has changed with farmers. In the past pesticides and fertilizers were typically applied separately, but due to time constraints and fuel costs they are being combined and applied in one tank mixes. The ionic strength of the fertilizer solution leads to incompatibilities due to a reduction in the solubility of the surfactants/adjuvants in the pesticide formulation. One way to modify the solubility properties within a formulation and/or to improve the mixing and dispersion of the formulation into the fertilizer is to incorporate a hydrotrope into the recipe. Examples of typical hydrotropes used would be sodium xylene sulfonate or phosphate esters. Both classes of chemistries have drawbacks; sodium xylene sulfonate is an environmental hazard and phosphates esters, due to its very low pH's, is difficult to be incorporated into the formulation at a level high enough to be effective when diluted into the fertilizer. Additionally, the high acidity of phosphate ester makes it unsuitable for use in formulation containing ether sulfate as adjuvant, since it would result in the hydrolysis of the ether sulfate.

The objective of the present invention is, therefore, to find a new agricultural hydrotrope that is efficient in formulating agricultural compositions, which compositions will remain homogeneous upon dilution, and stable, with improved activity. These and other objects are achieved by the formulations of the present invention.

SUMMARY OF THE INVENTION

Accordingly, the present invention is based on the discovery of a pesticide formulation comprising

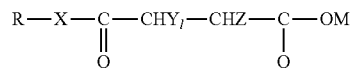

R is a linear or branched alkyl group comprising 3-8 carbons;
X is oxy (O), amino (NH) or alkylamino (R'N, where R'=linear or branched alkyl group with 1-4 carbons);
Y and Z can be the same or different and comprise: hydrogen (H), or sulfonate salt (—SO$_3$M' where M'=sodium, ammonium, potassium, or calcium); and
M may be sodium, ammonium, potassium, calcium, light amine (ethylamine, propylamine, isopropylamine), or alkanolamine (ethanolamine, or diethanolamine, triethanolamine)

The invention is further directed to a method of providing pesticide protection to an agricultural crop by applying the formulation of claim 1 to the crop.

Other embodiments of the invention concern details related to adjuvants and other ingredients of the pesticide formulation, all of which are described in detail below.

BRIEF DESCRIPTION OF THE DRAWINGS

FIG. 1 comprises three pictures showing glass containers filled with aqueous mixtures of glufosinate-ammonium formulations with and without the hydrotrope of the invention.

FIG. 2 is a ternary diagram showing regions of varying percentages of separation of aqueous mixtures of pesticide, adjuvant and monobutyl sulfosuccinate as hydrotrope.

DETAILED DESCRIPTION OF THE INVENTION

With regard to formula I, the preferred formula is a monoalkyl sulfosuccinate hydrotrope having the structure:

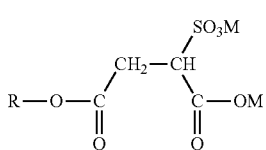

Where R: C3-C8 alkyl group, and M: sodium, potassium, or ammonium ion. Sodium is the most common salt. Typically, sodium monoalkylsulfosuccinates (IB) are prepared by two consecutive reactions: reaction of the selected alcohol with maleic anhydride, and addition of sodium sulfite to the resulting ester acid (IA)

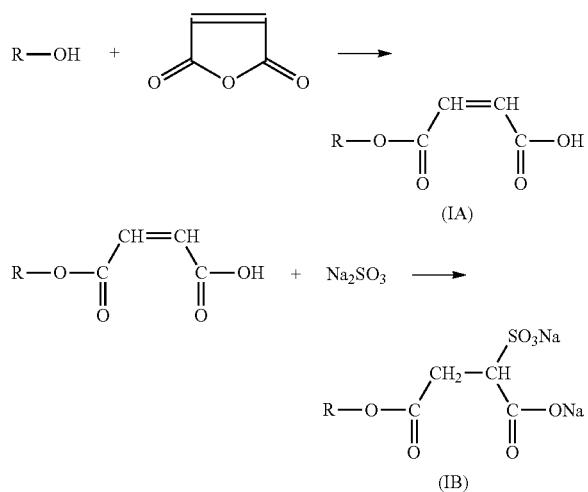

Compared to the conventional hydrotropes such as sodium xylene sulfonate and phosphate esters, monoalkylsulfosuccinates are desirable in every way. Their preparation requires simple process and simple equipment. Unlike sodium xylene sulfonate, monoalkylsulfonates are environmental friendly; they all are highly biodegradable. And unlike phosphate esters, they are mild to skin and eyes, and do not cause undesired/unwanted chemical decomposition of other components of the herbicide/pesticide formulations. But most important of all, their performance as hydrotropes is at least equal, and often times superior, to that of the conventional ones.

Suitable herbicides include acetochlor, acifluorfen, aclonifen, alachlor, ametryn, amidosulfuron, aminopyralid, amitrole, anilofos, asulam, atrazine, azafenidin, azimsulfuron, benazolin, benfluralin, bensulfuron-methyl, bentazone, bifenox, binalafos, bispyribac-sodium, bromacil, bromoxynil, butachlor, butroxidim, cafenstrole, carbetamide, carfentrazone-ethyl, chloridazon, Chlorimuron-ethyl, chlorobromuron, chlorotoluron, chlorsulfuron, cinidon-ethyl, cinosulfuron, clethodim, Clomazone, Clopyralid, Cloransulam-methyl, Clorsulfuron, Cyanazine, Cycloate, Cyclosulfamuron, Cycloxydim, Dalapon, Desmedipham, Dicamba, Dichlobenil, Dichlormid, Diclosulam, Diflufenican, Dimefuron, Dimepipeate, Dimethachlor, Dimethenamid, Diquat, Diuron, Esprocarb, Ethalfluralin, Ethametsulfuron-methyl, Ethofumesate, Ethoxysulfuron, Fentrazamide, Flazasulfuron, Florasulam, Fluchloralin, Flufenacet, Flumetsulam, Flumioxazin, Fluometuron, Flupyrsulfuron-methyl, Fluorochloridone, Fluoroxypyr, Flurtamone, Fomesafen, Foramsulfuron, Glufosinate, Hexazinone, Imazamethabenzm, Imazamox, mazapic, Imazapyr, Imazaquin, Imazethapyr, Imazosulfuron, Iodosulfuron, Ioxynil, Isoproturon, Isoxaben, Isoxaflutole, Lactofen, Lenacil, Linuron, Mefenacet, Mesosulfuron-Methyl, Mesotrione, Metamitron, Metazachlor, Methabenzthiazuron, Metobromuron, Metolachlor, Metosulam, Metoxuron, Metribuzin, Metsulfuron-methyl, Molinate, MSMA, Napropamide, Nicosulfuron, Norflurazon, Oryzalin, Oxadiargyl, Oxadiazon, Oxasulfuron, Oxyfluorfen, Paraquat, Pendimethalin, Phenmedipham, Picloram, Pretilachlor, Profoxydim, Prometryn, Propanil, Propisochlor, Propoxycarbazone, Propyzamide, Prosulfocarb, Prosulfuron, Pyraflufen-ethyl, Pyrazosulfuron, Pyridate, Pyrithiobac, Quinclorac, Quinmerac, Rimsulfuron, Sethoxydim, Simazine, S-Metolachlor, Sulcotrione, Sulfentrazone, Sulfosulfuron, Tebuthiuron, Tepraloxydim, Terbuthylazine, Terbutryn, Thifensulfuron-methyl, Thiobencarb, Tralkoxydim, Tri-allate, Triasulfuron, Tribenuron-methyl, Triclopyr, Trifloxysulfuron, Trifluralin, Triflusulfuron-methyl, Tritosulfuron, and mixtures and combinations thereof. Preferred herbicides are Acetochlor, Atrazine, Dicamba, Glufosinate, Paraquat, 2,4-D and mixtures and combinations thereof. More preferred herbicides are 2,4-D, Atrazine, Dicamba, and Glufosinate and mixtures and combinations thereof. The most preferred herbicide is glufosinate-ammonium. When the herbicide is an acid, it can be used in the acid form, though it is preferred that the herbicide be in the salt form selected from at least one of the group of an amine, lithium, sodium, ammonium or potassium. It shall be pointed out that when a pesticide appears in the text as a general name without specifying the counterions, it means both its acid form and salt form through out the specification.

Another embodiment of the present invention is a fungicide formulation containing the hydrotropes of the present invention. Examples of suitable fungicides are:

Acibenzolar-S-methyl, aldimorph, amisulbrom, anilazine, azaconazole, azoxystrobin, benalaxyl, benodanil, benomyl, benthiavalicarb, binapacryl, biphenyl, bitertanol, blasticidin-S, boscalid, bromuconazole, bupirimate, captafol, captan, carbendazim, carboxin, carpropamid, chloroneb, chlorothalonil, chlozolinate, copper, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, dinocap, dithianon, dodemorph, dodine, edifenphos, enestrobin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumorph, fluopicolide, fluoxastrobin, fluquinconazole, flusilazole, flusulfamide, flutolanil, flutriafol, folpet, fosetyl-Al, fthalide, fuberidazole, furalaxyl, furametpyr, guazatine, hexaconazole, hymexazole, imazalil, imibenconazole, iminoctadine, iodocarb, ipconazole, iprobenfos (IBP), iprodione, iprovalicarb, isoprothiolane, isotianil, kasugamycin, kresoxim-methyl, laminarin, mancozeb, mandipropamid, maneb, material of biological, mepanipyrim, mepronil, meptyldinocap, metalaxyl, metalaxyl-M, metconazole, methasulfocarb, metiram, metominostrobin, metrafenone, mineral oils, organic oils, myclobutanil, naftifine, nuarimol, octhilinone, ofurace, origin, orysastrobin, oxadixyl, oxolinic acid, oxpoconazole, oxycarboxin, oxytetracycline, pefurazoate, penconazole, pencycuron, penthiopyrad, phosphorous acid and, picoxystrobin, piperalin, polyoxin, potassium bicarbonate, probenazole, prochloraz, procymidone, propamocarb, propiconazole, propineb, proquinazid, prothiocarb, prothioconazole, pyraclostrobin, pyrazophos, pyribencarb, pyributicarb, pyrifenox, pyrimethanil, pyroquilon, quinoxyfen, quintozene (PCNB), salts, silthiofam, simeconazole, spiroxamine, streptomycin, sulphur, tebuconazole, teclofthalam, tecnazene (TCNB), terbinafine, tetraconazole, thiabendazole, thifluzamide, thiophanate, thiophanate-methyl, thiram, tiadinil, tolclofosmethyl, tolylfluanid, triadimefon, triadimenol, triazoxide, tricyclazole, tridemorph, trifloxystrobin, triflumizole, triforine, triticonazole, validamycin, valiphenal, vinclozolin, zineb, ziram, and zoxamide, and mixtures and combinations thereof.

Still another embodiment of the present invention is an insecticide formulation containing the hydrotropes of the present invention. Examples of suitable insecticides are: kerosene or borax, botanicals or natural organic compounds (nicotine, pyrethrin, strychnine and rotenone), chlorinated hydrocarbon (DDT, lindane, chlordane), organophosphates (malathion and diazinon), carbamates (carbaryl and propoxur), fumigants (naphthalene) and benzene (mothballs), synthetic pyrethroids, and mixtures and combinations thereof.

The above listings of specific pesticides are not intended to be inclusive of all possibilities.

Yet still another embodiment of the present invention is a mixture of any herbicide, fungicide, and insecticide selected form the above groups containing the hydrotropes of the present invention.

Performance of Monosulfosuccinates as Hydrotropes

The unique structure of the monoalkyl sulfosuccinates of structure (I) renders them the capability of compatibilizing or stabilizing the highly concentrated components in the pesticide/herbicide formulation. Such capability is best illustrated by the performance of monoalkylsulfosuccinates, particularly of sodium monobutyl sulfosuccinate in the high load glufosinate-ammonium formulations. In these formulations, the active loading is at the highest (280 g/l). As the active content increases, the adjuvant content increases and the water content is reduced. Consequently, there is not enough water to solubilize both the herbicide active and the adjuvant. Without the action of a hydrotrope, the two components would separate.

FIG. 1 shows the stability and uniformity of highload formulation containing 1:1 mixture glufosinate-ammonium active and ACAR 7053—a highly concentrated C8 ether sulfate used in the formulation as adjuvant. Without hydrotrope, the formulation is a hazy mixture when freshly mixed (FIG. 1A) that separates into two layers upon standing (FIG. 1B). In the presence of monobutylsulfosuccinate, which serves as a compatibilizing agent, the formulation is clear when freshly mixed, and retains that clarity and uniformity after prolonged standing (FIG. 1C)

The performance of the sodium monobutyl sulfosuccinate as hydrotrope for pesticide formulation containing the AGAR 7053 as adjuvant was also confirmed by the results of a designed experiment. As illustrated in FIG. 2, the sulfosuccinate performed as a hydrotrope over a wide range of concentrations.

The numbers associated with the small colored bar in the upper left hand corner of the Figure give the percentage of separation in the samples. The colors in the bar are related to the colored regions in the ternary diagram. As the regions in the graph go from red to blue the percentage of separation goes to zero.

The performance of the hydrotropes of the invention are at least equal, and often times superior, to conventional hydrotropes, but in any event would be preferred because the hydrotropes of the invention are simple to prepare, are environmentally friendly and biodegradable. Sulfosuccinates are typically used as wetting agents, particularly dialkylates, e.g. di-2ethylhexylsulfosuccinate, which have fairly low water solubility. It is quite surprising, therefore, that the sulfosuccinates of the invention are such effective hydrotropes.

The surfactants of the present invention can be used as a tank-mix additive or formulated in an in-can formulation. They are suitable in a solid pesticide formulation and, particularly, in a liquid pesticide formulation.

Other additives can be present in the formulations containing the adjuvant/surfactants of the present invention. They are defoamer, diluents, compatibility agents, biocides, thickeners, drift control agents, dyes, fragrance, and chealating agents. The use of a compatibility agent is particularly important if the nitrogen containing surfactant of the present invention is not very compatible in concentrated pesticide formulations. When using a compatibility agent, it is advantageous that the compatibility agent is a surfactant which can also enhance the efficacy of the pesticide. One such a preferred compatibility agent is C6-C12 dimethyamidopropylamine.

The temperature range during application of the pesticide formulation of the invention is not critical and would vary based on crop and geographical region.

There is also no critical degree of application of the formulation. That would depend on the particular crop and pesticide employed, and could also vary considerably.

We claim:

1. A pesticide formulation comprising a pesticide, an adjuvant and a monoalkyl sulfosuccinate hydrotrope having the structure:

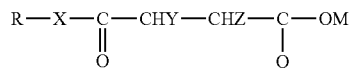

where
R is a linear or branched alkyl group comprising 3-4 carbons;
X is O;
Y and Z, independently of one another, comprise H or —SO$_3$M' where M'=sodium, ammonium, potassium, or calcium, wherein at least one of Y and Z comprises —SO$_3$M'; and
M is a sodium, ammonium, potassium, calcium, ethylamine, propylamine, isopropylamine, or alkanolamine;
wherein a weight ratio of pesticide to adjuvant is about 1:1 to about 1:5.

2. The pesticide formulation of claim 1, wherein the monoalkyl sulfosuccinate hydrotrope has the structure

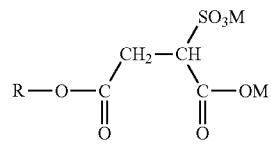

where R is a C3-C4 alkyl group, and M is a sodium, potassium, or ammonium ion.

3. The pesticide formulation of claim 1 wherein the pesticide is glufosinate-ammonium.

4. The pesticide formulation of claim 1, wherein R is a linear or branched alkyl group comprising 4 carbons.

5. The pesticide formulation of claim 1, wherein the hydrotrope is a sodium monobutylsulfosuccinate.

6. A method of providing pesticide protection to an agricultural crop comprising the step of applying the formulation of claim 1 to said crop.

7. The method of claim 6 wherein the pesticide is glufosinate-ammonium.

8. A pesticide formulation comprising a pesticide, an adjuvant and a monoalkyl sulfosuccinate hydrotrope having the structure:

where

R is a linear or branched alkyl group comprising 3-4 carbons;

X is O;

Y and Z, independently of one another, comprise: H, or —SO$_3$M' where M'=sodium, ammonium, potassium, or calcium, wherein at least one of Y and Z comprises —SO$_3$M'; and M is sodium, ammonium, potassium, calcium, ethylamine, propylamine, isopropylamine, or alkanolamine;

wherein the adjuvant comprises a sodium or ammonium salt of an alcohol ether sulfate; and wherein a weight ratio of pesticide to adjuvant is about 1:1 to about 1:5.

9. The pesticide formulation of claim 8, wherein the monoalkyl sulfosuccinate hydrotrope has the structure:

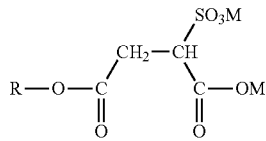

where R is a C3-C4 alkyl group, and M is a sodium, potassium, or ammonium ion.

10. The pesticide formulation of claim 8, wherein R is a linear or branched alkyl group comprising 4 carbons.

11. The pesticide formulation of claim 8, wherein the hydrotrope is a sodium monobutylsulfosuccinate.

12. A method of providing pesticide protection to an agricultural crop comprising the step of applying the formulation of claim 8 to said crop.

13. A pesticide formulation comprising a pesticide, an adjuvant and a monoalkyl sulfosuccinate hydrotrope having the structure:

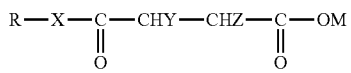

where

R is a linear or branched alkyl group comprising 3-4 carbons;

X is O;

Y and Z, independently of one another, comprise H, or —SO$_3$M' where M'=sodium, ammonium, potassium, or calcium, wherein at least one of Y and Z comprises —SO$_3$M'; and M may be sodium, ammonium, potassium, calcium, ethylamine, propylamine, isopropylamine, or alkanolamine;

wherein the pesticide is glufosinate-ammonium;

wherein the adjuvant is a sodium or ammonium salt of an alcohol ether sulfate; and wherein a weight ratio of pesticide to adjuvant is from about 1:1 to about 1:5.

14. The pesticide formulation of claim 13, wherein the monoalkyl sulfosuccinate hydrotrope has the structure:

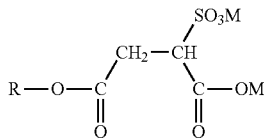

where R is a C3-C4 alkyl group, and M is a sodium, potassium, or ammonium ion.

15. The pesticide formulation of claim 13, wherein R is a linear or branched alkyl group comprising 4 carbons.

16. The pesticide formulation of claim 13, wherein the hydrotrope is a sodium monobutylsulfosuccinate.

17. A method of providing pesticide protection to an agricultural crop comprising the step of applying the formulation of claim 13 to said crop.

* * * * *